United States Patent
Schedel-Niedrig et al.

(10) Patent No.: US 6,212,253 B1
(45) Date of Patent: Apr. 3, 2001

(54) APPARATUS AND METHOD FOR X-RAY ABSORPTION SPECTROSCOPY

(75) Inventors: Thomas Schedel-Niedrig; Axel Knop-Gericke; Michael Havecker, all of Berlin (DE)

(73) Assignee: Max-Planck-Gesellschaft, Berlin (DE)

( * ) Notice: Subject to any disclaimer, the term of this patent is extended or adjusted under 35 U.S.C. 154(b) by 0 days.

(21) Appl. No.: 09/266,015

(22) Filed: Mar. 11, 1999

(30) Foreign Application Priority Data

Mar. 3, 1998 (DE) .............................................. 198 10 539

(51) Int. Cl.[7] .................................................. G01N 23/227
(52) U.S. Cl. ................................................. 378/53; 378/57
(58) Field of Search .................................. 328/51, 53, 58, 328/64, 45

(56) References Cited

U.S. PATENT DOCUMENTS 4,573,008 * 2/1986 Lischke ............................. 324/158 R

OTHER PUBLICATIONS

"X–ray Spectroscopy at a Buried Diode Interface", IBM Technical Disclosure Bulletin, Dec. 1984, US, vol. 27, Issue No. 7B, pp. 4468–4469.*

"Analysis of Near–Surface Impurities Using Spectroscopy", IBM Technical Disclosure Bulletin, Dec. 1984, US, vol. 27, No. 7B, pp. 4455–4456.*

Moggridge et al., "Enviromental Cells for In Situ X–ray Diffraction and X–ray . . . Catalysts", Nucl. Instr. and Meth. In Phys. Res. B 97 1995, pp. 28–32.

Harris, "A Spinning Stage, Total Electron–Yield . . . Spectra", Rev. Sci, Instrum. 68(1), Jan. 1997, pp. 23–29.

* cited by examiner

*Primary Examiner*—David P. Porta
(74) *Attorney, Agent, or Firm*—Dennison, Scheiner, Schultz & Wakeman

(57) ABSTRACT

In order to investigate the reactants involved in a reaction between a gas and a solid by means of X-ray absorption spectroscopy an apparatus is provided which comprises, within a measuring chamber (2), a sample holder (23) for holding a sample (24) of the solid, means for forming an atmosphere of the gas in the measuring chamber under selectable pressure, a window (20) for the entry of X-rays for the irradiation of the sample (24) and a collector arrangement (21, 22) arranged spaced from the sample holder (23), in order to collect in the measuring chamber (2) electrons released by X-ray absorption. The collector arrangement comprises two collector electrodes (21 and 22) which are arranged mutually spaced from one another in sequence lengthwise along the X-ray path between the window (20) and the sample holder (23). Each collector electrode (21, 22) and the sample holder (23) have respective connection means (31, 32, 33) for the connection of each to a respective associated predetermined potential and for the separate measurement of the currents ($I_1, I_2, I_3$) flowing through these connections. By evaluation of these currents evidentially helpful spectra of the involved reactants can be obtained both at and adjacent to the sample surface and also in the gas phase within the range of soft X-rays.

30 Claims, 4 Drawing Sheets

APPARATUS AND METHOD FOR X-RAY ABSORPTION SPECTROSCOPY

BACKGROUND OF THE INVENTION

The invention relates to an apparatus for investigating the reactants involved in a reaction between a gas and a solid by means of X-ray absorption spectroscopy (XAS). The invention is also concerned with an XAS-method for investigating gas-solid reactions in situ using this apparatus.

For the investigation of gas-solid reactions and their reaction products it is frequently necessary to use spectroscopic techniques in which the intrusion of the probe and the disturbance of the reaction environment during the investigation is reduced to a minimum. This applies in particular to investigations in the field of heterogeneous catalysts. Here, in situ investigations are of particular significance. It has been established that ex situ or post mortem investigations which are not carried out under working conditions yield somewhat different results as compared with in situ investigations.

An apparatus and a method for the in situ investigation of catalytic agents by means of X-ray absorption spectroscopy is known for example from "Nuclear Instruments and Methods in Physics Research" B97 (1995) pages 28–32. The apparatus described there comprises a measuring cell with a sample holder for solid samples located in the cell and with a window for the entry of X-rays for the irradiation of the sample. The sample holder consists of a gold-coated plate of silica (silicon dioxide) which is arranged within a cylinder of the same material which is open at both ends. This cylinder, whose axis lies parallel to the direction of propagation of the X-rays, is biassed to a positive or negative potential with reference to the sample holder and serves as a collector arrangement for the collection of electrons which are emitted by the sample which is fixed to the sample holder as a result of the X-ray absorption. The electrical current which flows from the collector electrode to a ground connection is used as a measurement value for the plotting of the absorption spectrum. The principle belongs to the field of total electron yield detection (TEY detection), since only the total yield of electrons is determined, without analysis of their kinetic energy. Values >20V have been established as preferable for the potential difference between collector arrangement and sample holder. Investigations at pressures up to 1 atmosphere and at temperatures up to 500° C. in the range of middle and hard X-radiation ($\geq 4.5$ keV) have been carried out on samples such as methanol synthesis catalysts $Cu/ZnO/Al_2O_3$, a copper/nickel alloy as well as a nickel reforming catalyst.

Having regard to the aforementioned publication, further investigations are reported in "Faraday Discussions" 105 (1996) pages 317–336. There it is maintained that the TEY detection uses the proportionality between the absorption coefficient of the sample for X-ray radiation and the number of the Auger electrons emitted from the sample, with the TEY signal having a linear relationship to the absorption coefficient of the sample. In the book "Practical Surface Analysis" by D. Briggs and others (John Wiley, New York 1983) it had already been established that the average penetration depth of the most energetic Auger electrons from the sample determines the surface sensitivity, and that as a consequence the surface sensitivity of the TEY signal depends upon the energy of the absorption edge. It has been observed that the average penetration depth of a few nm for absorption edges with <1 keV changes to several hundred nm for X-ray energies >10 keV.

SUMMARY OF THE INVENTION

TEY X-ray absorption investigations under reaction conditions have until now been carried out only for elements with atomic numbers Z>15. It is the object of the invention to extend the apparatus for and a method of X-ray absorption spectroscopy with total electron yield detection (so-called TEY detection) so that, for in situ investigations of gas-solid reactions, evidential spectra can be obtained even for elements of lesser atomic numbers Z<15, and wherein, preferably, a high surface sensitivity at the solid sample should be achievable.

By the use in accordance with the invention of two sequentially arranged collector electrodes along the X-ray path in the gas atmosphere between the X-ray window and the solid sample, and by the possibility, created by means of suitable terminal devices, of separate current measurements at the two collector electrodes and at the sample holder, the respective total yields of the electrons originating from these three parts can be determined separately. By evaluation of the three measured currents, preferably in relation to the measured intensity of the X-rays directed at the window or passing through it, information about the X-ray absorption as well as at the surface of the solid and also in the gas atmosphere can be achieved.

This is advantageous in particular for the investigation of heterogenous catalyst processes. In such cases it is very desirable to monitor the catalytic activity of a sample simultaneously with the changes in the gas composition, since a close connection has been established between the spectra of gas and the chemical binding state at the surface of the catalyst. Consequently, the study of heterogenous catalyst processes is preferred, even if not exclusively the field of use of the invention.

In order specially to augment the strength of the evidence of the data detectable by means of the invention, in a preferred embodiment, the construction and position of the collector electrode which is closer to the sample holder is so chosen that it effectively screens in terms of measurement a solid sample held by the sample holder from electrons coming from the space between the two collector electrodes, while simultaneously the other collector electrode which is further from the sample is effectively screened in terms of measurement from electrons coming from the space next to the sample. By this means, a particularly clear differentiation is possible between the X-ray absorption in the gas phase and the X-ray absorption at the surface of the sample.

With embodiments of the present invention it is possible for the first time successfully to investigate gas-solid reactions in situ for atoms of low atomic number, such as carbon, nitrogen and oxygen, using soft X-rays in the energy range of 100 to 1000 eV under high gas pressures up to 25 mbar and sample temperatures up to 1000° K., and indeed with low expenditure in terms of apparatus. The achievable results can be optimised if, in a preferred embodiment of the invention, measures are adopted in order selectively to bias at least the collector electrode which is closer to the sample to a positive potential relative to the other collector electrode and to the sample holder, and/or to adjust the distance between the collector electrode which is closer to the sample and the sample holder.

BRIEF DESCRIPTION OF THE DRAWINGS

The invention will now be described in more detail with reference to an embodiment which is given by way of example and with reference to drawings, in which the following representation serves only for the purposes of illustration and the features given by way of example, as well as the combinations of features in the subsidiary claims, are not to be considered as limiting the invention. In the drawings:

DESCRIPTION OF THE PREFERRED EMBODIMENT

Figure 1:
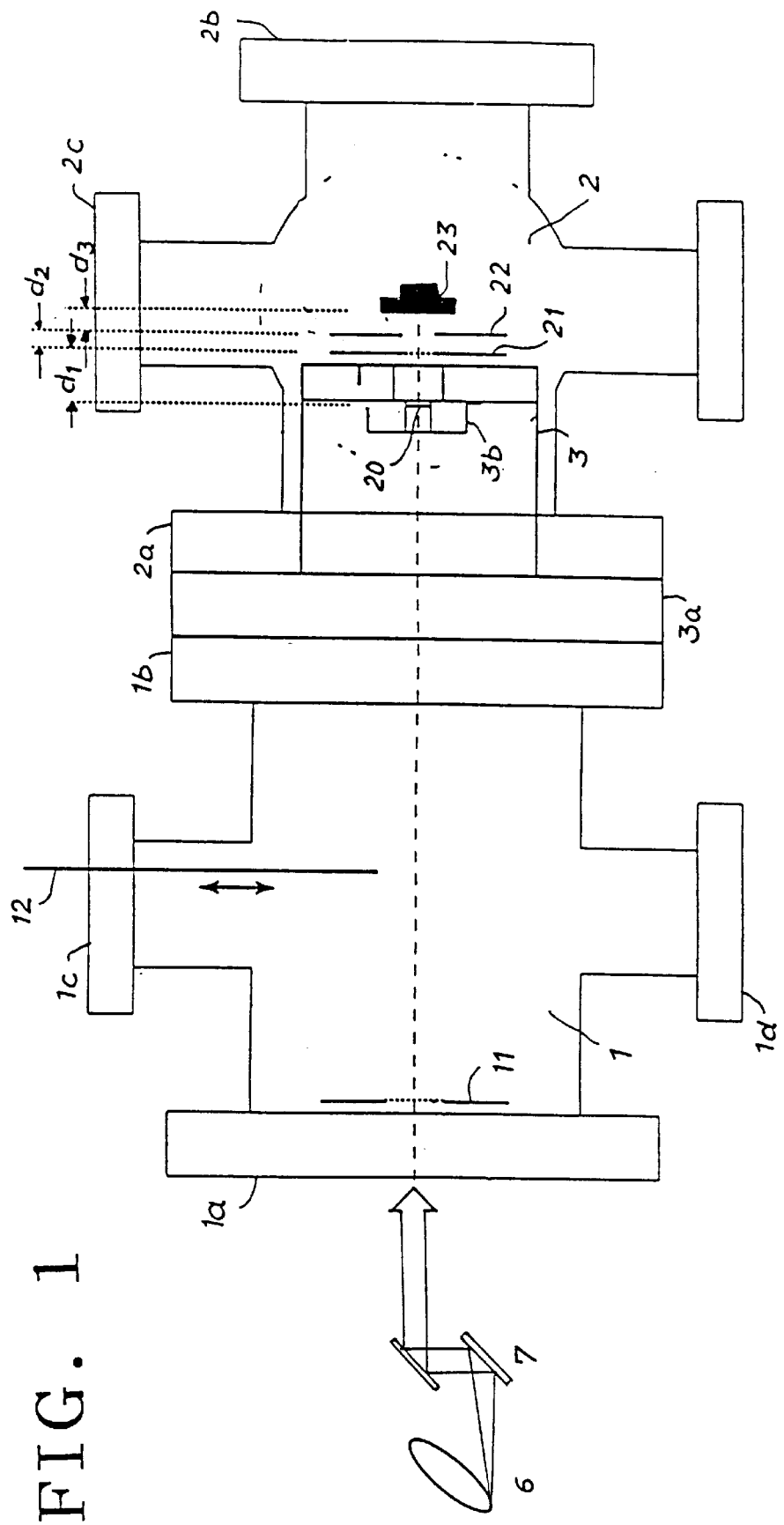
FIG. 1 is a schematic illustration of a measuring chamber with essential parts of an apparatus according to the invention and a UHV-chamber connected in advance of it for connection to an X-ray source.

The schematic illustration in FIG. 1 shows, in the right-hand half, as a cross-sectional view, a measuring chamber 2, and in the left-hand half an ultra high vacuum chamber (UHV chamber) 1 for the connection of the measuring chamber 2 to an X-ray source. In the view shown in FIG. 1 the X-rays travel from the left-hand input of the UHV chamber 1 in the plane of the drawing to the right, towards the measuring chamber 2. For both chambers 1, 2 the same basic structure can be used, for example each can be a stainless steel chamber designed for ultra high vacuum, with four connecting flanges 1a, 1b, 1c, 1d and 2a, 2b, 2c, 2d. The left-hand end of the UHV chamber is connected by means of a UHV flanging and by means of an X-ray monochromator 7 to an X-ray source, such as the beam output tube of the storage ring of a synchrotron 6, preferably by means of a 100 mm standard flange (Conflat flange CF 100). The UHV chamber 1 contains a conventional monitor 11 for the X-ray intensity $I_0$ which enters into the chamber by way of the monochromator 7. The X-ray monitor 11 is preferably a copper grating with gold vapor-deposited thereon with a diameter of about 20 to 30 mm, with a fineness of about 40 lines per cm (100 lpi) and a permeability of about 95%. In the UHV chamber 1 there is also located a movable masking device 12 for the X-rays, in order to protect an ultra-thin X-ray window 20, through which the X-rays enter into the measuring chamber 2, from the "white light" (radiation of zeroth order) of the synchrotron 6 when the chamber is being set up.

The left-hand end of the measuring chamber 2 is connected to the right-hand end of the UHV chamber 1 by means of UHV standard flanges 1b, 2a (likewise CF 100). In the measuring chamber 2 are located four main elements which are arranged one after the other in the direction of the incoming X-rays. First, there is the window 20 for the incoming X-rays, then an oxidation-resistant first collector electrode 21, then an oxidation-resistant second collector electrode 22, and finally a holder 23 for a solid sample.

The window 20 is preferably an ultra-thin membrane consisting of a single-layer polyimide foil with a thickness of about 250 nm, which is provided on both sides with an aluminum-nitride layer of about 30 nm and additionally on one side with an aluminum layer of about 50 nm. Such a window is known per se and is commercially available (from the company Metorex International Oy, Finland) and has already been provided for use worldwide. For soft X-rays in the range of 100 eV to 1000 eV it has a permeability of approximately 2% to approximately 60% (i.e. approximately 2% at 100 eV and approximately 60% at 1000 eV). For the present invention the membrane is preferably supported by a polyimide grating and a tungsten grating. The window is vacuum tight, with the pressure-side surface arranged facing the atmosphere in the measuring chamber 2. The vacuum strength of such a window is high, for helium with a total gas pressure of 1100 mbar in the measuring chamber there results a leakage rate of less than $5*10^{-8}$ mbar*l/s in the UHV chamber. The window 20 is glued in front of the central opening of a 16 mm flange 3b which is fixed to the base of a cylinder 3 in the middle of a stainless steel flange 3a, said cylinder projecting into the measuring chamber 2 from the flange connection between the two chambers 1 and 2, as is shown in FIG. 1.

The oxidation-resistant first collector electrode 21 comprises a gold-coated copper grating which has a fineness of about 40 lines per cm (100 lpi), a diameter of 30 mm and a permeability of about 95% and which lies in the path of the X-rays coming through the window 20. The copper grating is upheld by a nickel plate which has a corresponding hole (diameter approximately 30 mm). Since the grating absorbs a small proportion of the X-rays, the current derivable from the first collector electrode contains a component which depends directly upon the intensity of the X-rays penetrating through the window 20. This can be utilised in a manner which will be described in more detail hereinafter.

The first collector electrode 21 is followed at a distance $d_2$, which is preferably substantially smaller than the distance $d_1$ between the window 20 and the first collector electrode 21, by a second collector electrode 22 which is provided with a central opening for the passage of the X-rays.

The second collector electrode 22 consists of a nickel foil having a thickness of 0.25 mm, which has an ultra-thin surface layer of natural oxide. Following the second collector electrode 22, seen in the direction of propagation of the X-rays, and at a certain distance $d_3$ there is the sample holder. This distance $d_3$ is preferably variable, for example within a range between one and four times the distance $d_2$ between the two collector electrodes 21, 22. The distance $d_3$ is preferably set so that X-rays still reach the sample and consequently an absorption signal can be measured which naturally depends upon the gas pressure in the measuring chamber and upon the intensity of the X-rays appearing in the chamber. If this intensity lies in the range of $10^{10}$ to $10^{11}$ photons per second and the overall distance from the window 20 to the sample lies for example in the range of 20 to 50 mm, then the total gas pressure should not amount to more than 25 mbar.

Figure 2:
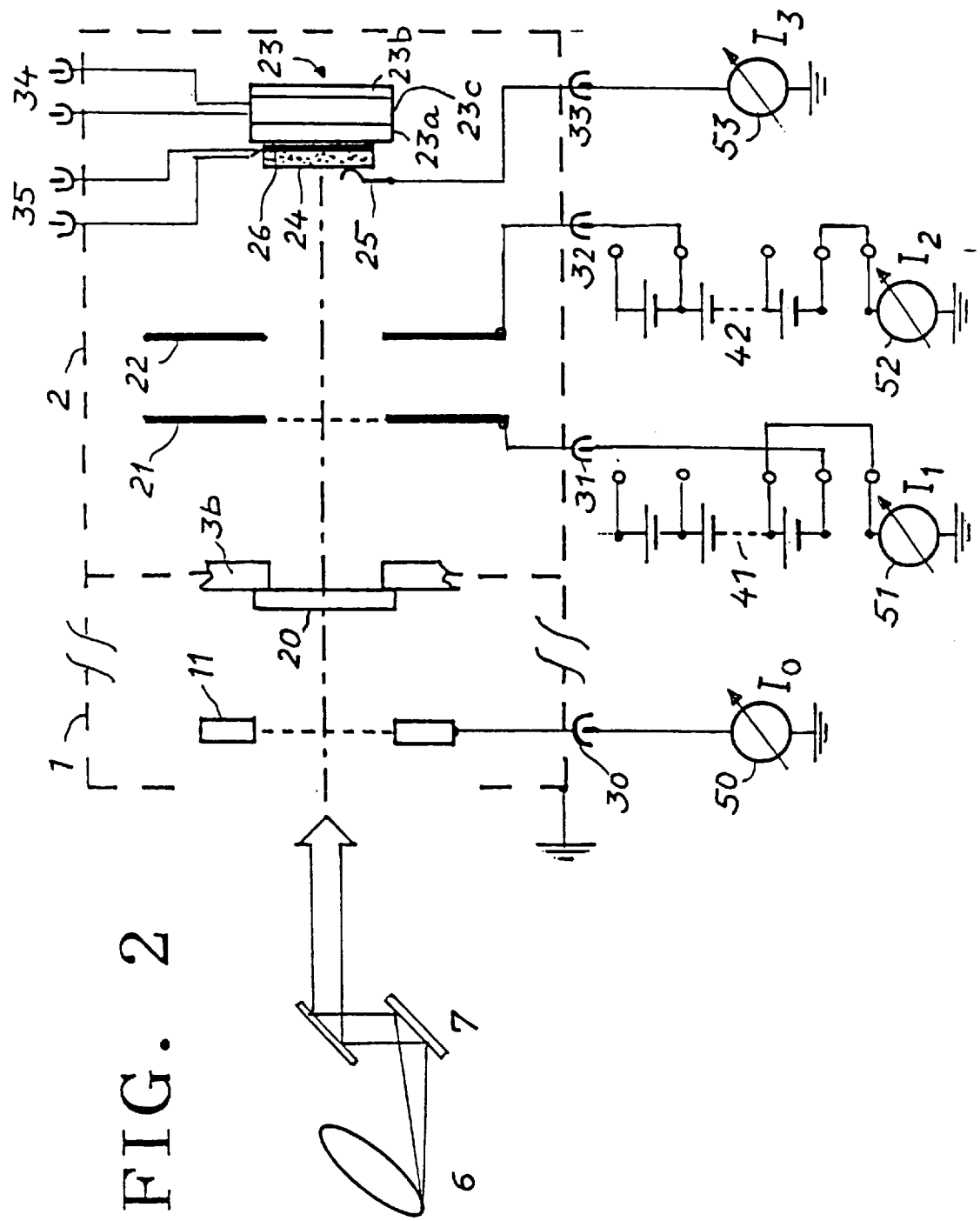
FIG. 2 schematically shows essential components of a measuring arrangement which includes the apparatus according to the invention.

As is shown more clearly in FIG. 2, in which the boundaries of the two chambers 1, 2 are only shown in outline by broken lines, the sample holder 23 comprises an electrically insulating and preferably thermally conductive plate 23a, for example of aluminum nitride with a thickness of about 1.5 mm and a surface dimension of 25×25 mm². On the rear side of this plate 23 is fixed a further plate 23b by means of four screws at the corners. This further plate 23b is preferably of boron nitride having a thickness of about 4 mm and the same surface dimensions as the aluminum nitride plate 23a. At least one metal clamp 25 is also provided, preferably of nickel or of the sample material, in order to hold the solid sample 24 firmly on the sample holder 23 and moreover to provide an electrical contact to the sample 24. Between the aluminum nitride plate 23a and the boron nitride plate 23b there is preferably provided a graphite plate 23c coated with boron nitride, which can serve as a resistance heater for heating the sample 24 up to about 1000° K. It is alternatively possible to use the graphite plate 23c alone as the sample holder, that is without the plates 23a and 23b. In order to measure the sample temperature, a temperature measuring instrument can also be provided, for example in the form of a thermal element 26 fixed directly to the rear side of the sample. The whole sample holder 23 preferably sits on a manipulator (not shown) by means of which both the distance $d_3$ to the second collector electrode 22 and also the polar angle of inclination of the sample surface relative to the incoming X-rays can be adjusted.

Two of the remaining flanges of the measuring chamber 2, preferably the flanges 2c and 2d which are shown in FIG. 1 at the upper and at the lower ends, are provided with devices for the introduction and removal of gaseous reactants such as $O_2$, He, Ar, $CH_3OH$, together with a device for the measurement and control of the total gas pressure in the measuring chamber as well as a device for gas analysis. These devices can be of conventional type and are therefore not shown separately in FIG. 1. Preferably, a Bayard-Alpert ion measuring head and a cold cathode are used for the pressure measurement, while the gas analysis can be effected by means of a mass spectrometer.

The investigations can be carried out under static or dynamic gas conditions. Static experiments track the changes in a volume of gas introduced into the measuring chamber, while dynamic experiments take place with a flow of gas.

In one practical embodiment of the invention the measuring chamber 2 can be designed for a volume of about 4 liters. The chambers 1, 2 also contain vacuum-tight feedthroughs for the electrical connection of the X-ray monitor 11, the collector electrodes 21, 22, the sample 24, the heater 23c and the temperature meter 26 to external electrical devices. These feedthroughs can be welded in vacuum-tight manner to free flanges of the chambers. In FIG. 2, these feedthroughs are shown purely symbolically as plug sockets 30, 31, 32, 33, 34, 35.

For the carrying out of a method of X-ray absorption spectroscopy in accordance with the invention, the chamber structure shown in FIG. 1 has the left-hand flange 1a of the UHV chamber 1 connected to a source 6 of soft X-rays, such as the storage ring of a synchrotron, with the energy range of the X-radiation being variable by means of the monochromator 7 from about 100 up to about 1000 eV. The two chambers 1, 2 are evacuated, e.g. by a turbomolecular pump, independently of one another down to a basic pressure of $5*10^{-9}$ mbar, after they have been heated for eight hours at 400° K. A measuring instrument 50 is connected by means of the associated terminal 30 to the X-ray monitor 11 at the input of the UHV chamber 1. This measuring instrument 50 directs to ground a current flow $I_0$ indicting the intensity of the X-radiation entering into the UHV chamber 1. The housings of the chambers 1 and 2 are maintained at ground potential.

The first collector electrode 21 is placed at a fixed potential $U_1$ relative to ground, preferably in the range of 0 to −15 V, for example as shown in FIG. 2 by connection of the associated socket 31 to an appropriate terminal of a battery 41. The opposite positive terminal of the battery 41 is connected to an appropriate ammeter 51, for example an instrument with current amplification of the type Keithley 427, in order to measure currents of the order of $10^{-8}$ amps relative to ground. The second collector electrode 22 is held at a preferably positive potential $U_2$ (<40V) relative to ground by means of the associated terminal 32 being connected to a similar arrangement of battery 42 and ammeter 52. Likewise, an ammeter 53, here again preferably of the Keithley 427 type, is connected to the nickel clamp 25 of the sample holder 23 by means of the associated terminal 33, with a potential $U_3$ of preferably 0 volt being maintained at the nickel clamp 25. The heating device 23c on the sample holder 23 is preferably connected by means of the associated terminals 34 to a suitable electrical supply circuit, with the thermal element 26 which monitors the temperature as a real value transducer being connected by way of the associated terminals 35 to a control circuit which controls the current supply to the heating device 23c in a manner to control the sample temperature.

The solid sample 24 arranged on the sample holder 23 and which has already been set in place before the evacuation of the measuring chamber 2 is first of all moved out of the X-ray path by means of a manipulator (not shown) which acts on the sample holder 23. After setting up the incoming X-radiation, the screen 12 in the UHV chamber is moved out of the beam corridor of the monochromator, the reactant gas is introduced into the measuring chamber 2, the sample 24 is brought into the path of the X-rays, and after the desired total gas pressure has been achieved in the measuring chamber 2 and the desired sample temperature has been achieved then the actual investigation can begin.

During the investigation the photon energy of the incoming X-rays is varied in the usual way over the particular region of interest. The currents derivable at the different terminals 30, 31, 32, 33 can be measured individually and simultaneously and can be registered and evaluated for the plotting of spectra. Under the influence of the X-radiation penetrating into the measuring chamber 2, the following described effects result.

After penetrating the window 20 the X-rays in the gas atmosphere within the chamber region between the window and the second collector electrode 22 produce Auger electrons by X-ray absorption, these arising by the Auger decay of the excited molecular state in the gas phase. The emitted electrons are partially inelastically scattered and subsequently are captured by the first collector electrode 21 and by the second collector electrode 22. The respective total yields are measured individually as current $I_1$ and current $I_2$ by means of the associated ammeters 51 and 52. The current $I_1$ contains in addition to this a component corresponding to the X-ray absorption at the grating of the first collector electrode 21.

In principle, in any gas, energy losses of the electrons occur through inelastic processes, even if a smaller X-ray absorption cross-section is observed for hydrogen and helium than for example for oxygen. As a data calculation by Peisert and Sauli, carried out many years ago, has shown (CERN 84-08, 1984), low-energy electrons can be collected over distances of approximately 10 mm at atmospheric pressures of about 100 mbar, by applying a bias potential of +45V to the collector electrode. This leads to the strong supposition that the signal $I_1$ of the total electron yield at the first collector electrode 21 is composed mainly of Auger electrons and secondary electrons which have been produced in the molecules of the gas phase by the X-ray absorption process.

The X-radiation appears subsequently through the central opening of the second collector electrode 22 and strikes finally against the sample surface, after traversing the gas path $d_3$ between the second collector electrode 22 and the sample 24. While the main portion of the electrons captured by the second collector electrode 22 are the aforementioned Auger and secondary electrons from the molecules of the gas phase, a smaller proportion are derived from the sample surface and the region close to the surface. The current $I_2$ measured by means of the second collector electrode 22 is accordingly composed of these components. The current $I_3$ derived from the sample 24 arises mainly from the X-ray absorption taking place in the sample. This current $I_3$ is substantially independent of other operating characteristics of the apparatus, since it has its origin almost exclusively in the electron emission from the sample surface and the region close to the surface generated by X-ray absorption.

The total gas pressure in the measuring chamber for a successful in situ X-ray absorption spectroscopy is limited by the X-ray absorption of the relevant gas phase in the overall path of the X-rays from the window 20 to the sample surface (range $d_1+d_2+d_3$). Effective investigations can be carried out with gas pressures up to 20 mbar for X-ray intensities of about $10^{10}$ photons per second, where the distance $d_1$ between the window 20 and the first collector electrode 21 is about 14 mm, the distance $d_2$ between the two collector electrodes 21, 22 is about 6 mm and the distance $d_3$ between the second collector electrode 22 and the sample surface is in the range of 5 to 23 millimetres. Typical values of the current $I_1$ then lie in the order of $10^{-8}$ ampere and higher for X-ray energies above the absorption edge by up to about the factor 5. Typical values for the total electron current $I_2$ lie in the order of $10^{-7}$ ampere and higher for X-ray energies above the absorption edge likewise by the factor 5. Typical values for the current $I_3$ lie in the range of a few nanoamperes.

Information about the X-ray structure of the reactants at the solid surface and in the region close to the surface can, as stated, be derived from the current $I_3$ from the sample 24 and from the current $I_2$ from the collector electrode 22 which is closer to the sample.

Information about the X-ray absorption of the gas phase can be obtained from the current $I_1$ of the collector electrode 21 which is further from the sample. This current $I_1$ can also be used in order to eliminate certain spectral artefacts which are produced in the measurement values of the currents $I_2$ and $I_3$ by the presence of the X-ray window 20, especially due to the dependence of the intensity of the transmitted radiation on the photon energy (so-called transmission function of the window). As has already been mentioned above, the current $I_1$ contains not only information about the gas phase, but also a component which, as a consequence of the X-ray absorption at the grating of the collector electrode 21, depends directly upon the X-ray intensity which passes through the window 20. Consequently, the aforesaid artefacts can be minimised by dividing the measurement value of $I_2$ and desirably also of $I_3$ by measurement values of $I_1$ which have been determined previously, preferably in vacuum or alternatively under (inert) gas conditions.

In order to eliminate the previously mentioned artefacts also in the evaluation of the current $I_1$ itself, the measurement values of $I_1$ received in situ are likewise preferably divided by the aforementioned $I_1$ values received under UHV conditions or inert gas conditions.

In the following, details and results of some experiments are described which have been carried out with the apparatus shown in FIGS. 1 and 2.

For the X-ray window 20, the two collector electrodes 21 and 22 and the sample holder 23, the structures, materials and dimensions described in more detail above were used. The distances $d_1$ and $d_2$ amounted to 16 mm and 6 mm. The distance $d_3$ was set to 5 mm.

As the source of X-rays the Berlin synchrotron BESSY was used, with an electron beam energy of 0.8 GeV and a toroidal grating monochromator with two gratings (1100 l/mm and 1500 l/mm). The photon energy scale was calibrated with an accuracy of plus or minus 0.5 eV, with the Cu—$L_3$ edge of a sample of pure polycrystalline copper serving as reference. The X-ray absorption spectroscopy experiments were carried out using the larger grating (1100 l/mm) of the monochromator, in the photon energy range of 250 to 1000 eV.

In all the experiments described hereinafter, polycrystalline copper, Cu(poly), was used as the solid sample. Before the experiments, the surface to be irradiated in the measuring chamber 2 was purified by subjecting it to a gas mixture of 98% helium and 2% hydrogen under a pressure of 10 mbar at 600° K. This process was repeated until, on examination by XAS under vacuum conditions, no contaminating carbon and oxygen components could any longer be detected.

In order to pick up the XAS spectra at the Cu—$L_{2,3}$ edge, the radiation of second order of the monochromator was used, in order to produce a better definition in the direction of the photon energy axis. The X-ray intensity at the output of the monochromator amounted to about $5*10^{10}$ photons per second. In the various experiments, the current $I_0$ at the X-ray monitor 11, indicating the radiation intensity, was measured, as were also the currents $I_1$ and $I_2$ derived from the first and second collector electrodes 21 and 22 and the current $I_3$ derived from the sample 24.

EXAMPLE 1

The sample was maintained at a temperature of 600° K. and was exposed to a methanol/oxygen gas mixture (mixture ratio 10:1) at a total pressure of 0.10 mbar. The bias potential amounted to 0V at the first collector electrode 21, +15V at the second collector electrode 22 and 0V at the sample.

Figure 3:
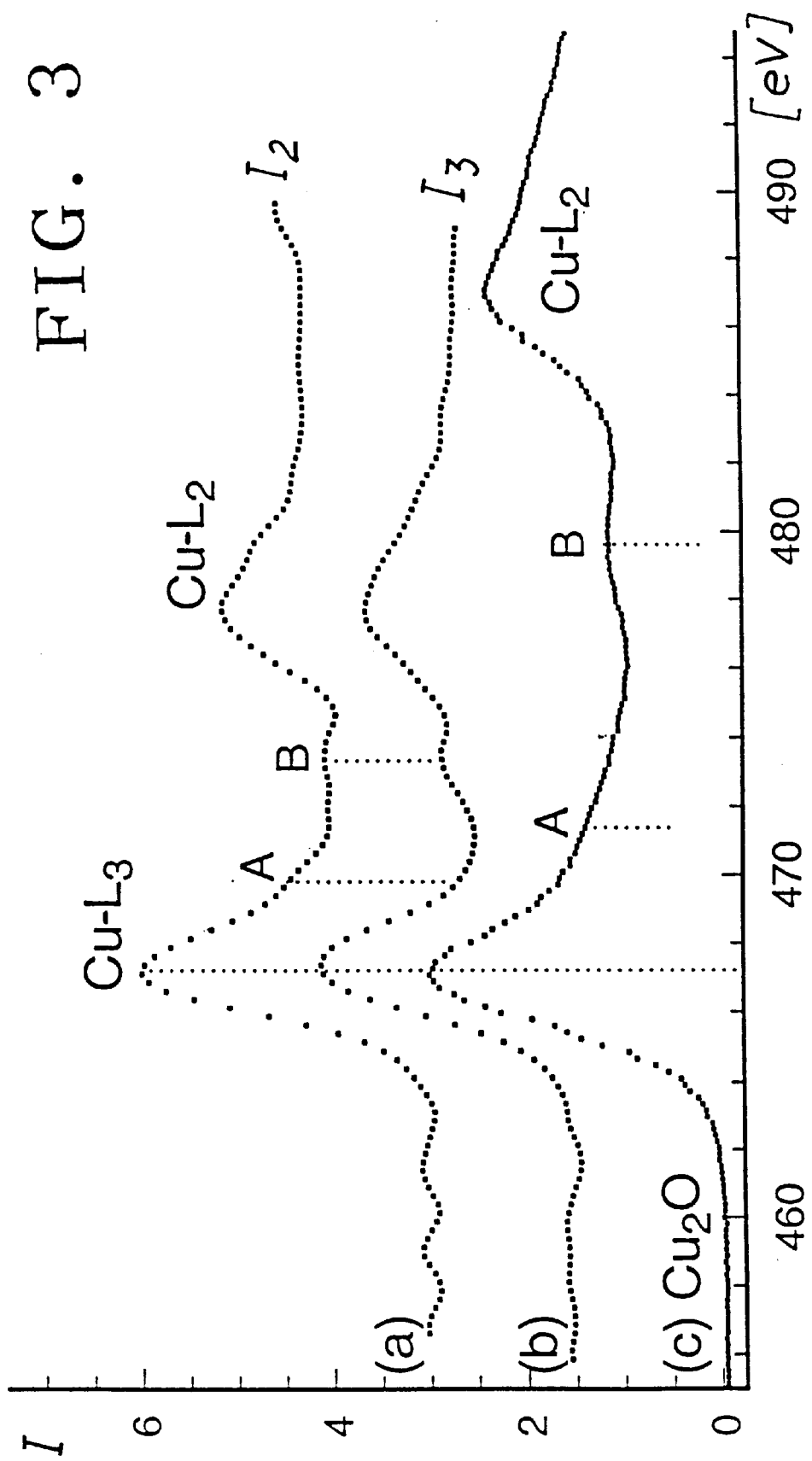
FIG. 3 to FIG. 6 show different X-ray absorption spectra which are obtainable by means of an apparatus according to the invention.

The spectra shown in FIG. 3 show the X-ray structures close to the absorption edges at the $L_2$ edge and at the $L_3$ edge of the copper (Cu—$L_{2,3}$ edges). The photon energy in eV for tuning of the monochromator is shown along the abscissa. The ordinate represents, in random measure, the particular measured current signals, normalised to the X-ray beam intensity $I_1$.

The curve (a) in FIG. 3 shows the spectrum of the current $I_2$ measured at the second collector electrode 22 (closer to the sample), while the curve (b) illustrates the spectrum of the current $I_3$ derived at the solid sample 24.

The curve (c) in FIG. 3 shows, in comparison, the X-ray structure at the Cu—$L_{2,3}$ edges of a $Cu_2O$ surface, as it was measured under UHV conditions, thus ex situ. This measurement was taken using a TEY detector working with two-stage electron multiplier, wherein indeed the radiation of first order from the monochromator was used, with a step resolution 3.0 eV for a photon energy of 930 eV. In order to be able to compare the spectrum thus obtained with the spectra (a) and (b) in FIG. 3 obtained by means of radiation of second order, the spectrum is indicated in this Figure with an abscissa displacement of −467 eV.

The most intensive structure in the spectra, occurring at the absorption edge, the "white line", can be used as an indicator for the copper(I) oxide $Cu_2O$, see for example the publication by Grioni et al in Phys. Rev. B45 (1992) page 3309. This line lies at 933.7 eV for radiation of first order and consequently between 466 and 467 eV for radiation of second order. The spectra (a) and (b) of FIG. 3 obtained in situ with the apparatus of the present invention show in this respect, as well as with respect to the intensity and shape of the most intensive line, a good correlation with the aforementioned publication by Grioni et al, and is also in harmony with the ex situ spectrum (c) of FIG. 3. Moreover, all other features A and B visible in spectrum (c) are observed in the spectra (a) and (b) of the in situ experiment. This confirms that from the signals $I_2$ and $I_3$ which are derivable in the apparatus of the present invention from the collector electrode 22 which is closer to the sample and from the sample 24 itself, powerful evidential results can be achieved from the sample surface and from the sample region close to the surface under reaction conditions.

EXAMPLE 2

A Cu(poly) foil was used as a sample, which was maintained at a temperature of 600° K. The collector electrode 22 closer to the sample was biased to +15V, the other bias potentials were 0V at the collector electrode 21 further from the sample and 0V at the sample 24. Investigations were made of the changes with time of the X-ray absorption structure close to the Cu—$L_{2,3}$ edges in an oxygen atmosphere by recording the current $I_2$ at the collector electrode 22 closer to the sample at time intervals of every ten minutes.

The experiment was carried out twice, under different oxygen pressures $P_{O2}$ of 0.10 mbar and 0.05 mbar.

Figure 4:
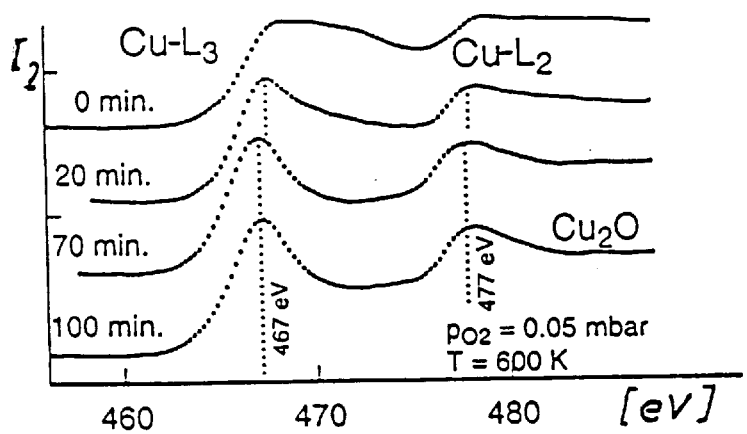

FIG. 4 shows the results under the oxygen pressure of $P_{O2}$=0.05 mbar. The upper curve represents the spectrum (0 min) detected at the outset, thus with a clean Cu(poly) sample. Under this are shown 3 spectra which were recorded after reaction intervals of 20 min, 70 min and 100 min respectively.

Figure 5:
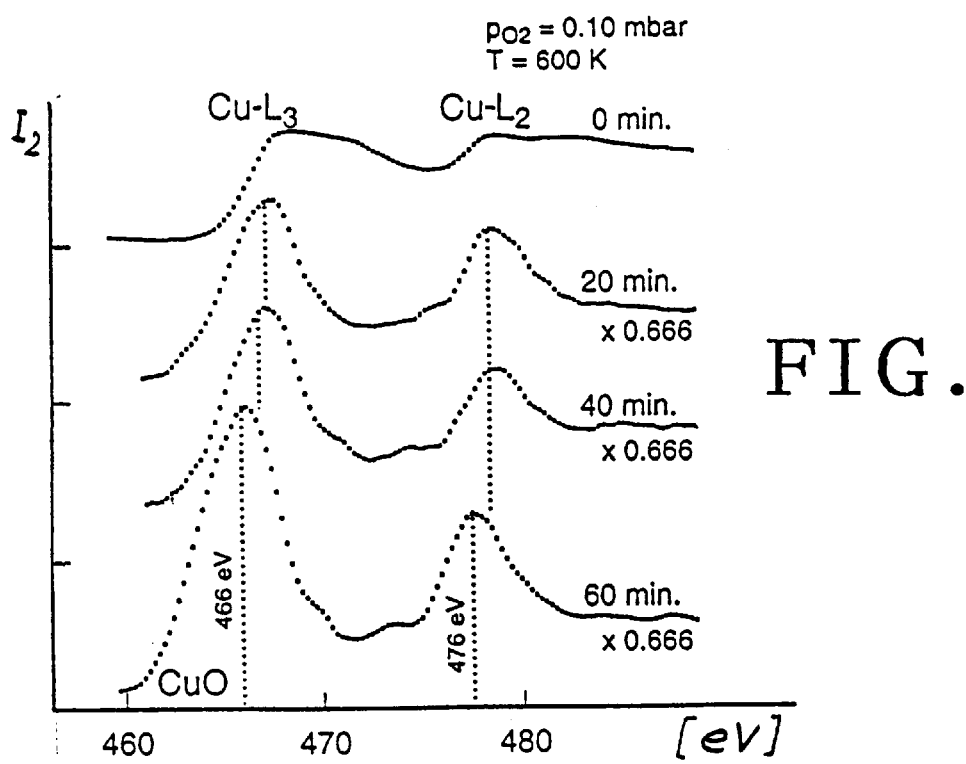

FIG. 5 shows the results under the oxygen pressure of $P_{O2}$=0.10 mbar. The upper curve represents the spectrum (0 min) recorded at the outset, thus with a clean Cu(poly) sample.

Below this are shown 3 spectra which were recorded after reaction times of 20 min, 40 min and 60 min respectively, where the ordinate values of these spectra are multiplied in relation to the top spectrum by the factor 0.666, in order to give greater clarity to the illustration.

As one can see in FIGS. 4 and 5, the overall shape of the spectrum changes even after a reaction time of a few minutes. In FIG. 4, there appears a significant intensive line at about 467 eV (Cu—$L_3$ edge) and again at about 477 eV (Cu—$L_2$ edge), by which the formation of copper(I) oxide $Cu_2O$ is indicated. After prolonged exposure to oxygen, in the case of FIG. 4 ($P_{O2}$=0.05 mbar) only a small intensification of the sharp lines is to be observed, while at the higher pressure according to FIG. 5 ($P_{O2}$=0.10 mbar) the intensity of the sharp lines increases rather more with increasing periods of exposure to the oxygen. Moreover, in the spectra according to FIG. 5, one can observe a displacement of the sharp lines in the direction of lower photon energy, to about 466 eV and about 476 eV. The oxidation process at the surface and in the region of the sample close to the surface is thus completely finished in the critical pressure range under investigation here after 60 min (FIG. 5) and after 100 min (FIG. 4), since after that no further changes to the spectra are to be observed, not even after 200 min.

The copper(II) oxide CuO and the copper(I) oxide $Cu_2O$ is characterised upon stimulation by radiation of first order by sharp lines at the positions approximately 931 eV and 934 eV respectively (for radiation of second order at positions approximately 466 eV and 467 eV respectively), and the intensity of these lines relative to the height of the absorption edges depends strongly upon the oxidation state of the copper (compare with the aforementioned publication by Grioni et al). Consequently, the copper oxide phases, as they are found after longer exposure to oxygen under the different pressures of 0.05 and 0.10 mbar, are reliably associated with the $Cu_2O$ and the CuO. This shows that measurements which are performed with an apparatus according to the invention by the recordal of the current $I_2$ derivable at the collector electrode 22 closer to the sample at different oxygen pressures, are a highly sensitive tool for the investigation in situ of the formation of copper oxide at the surface and in the region close to the surface.

EXAMPLE 3

Figure 6:
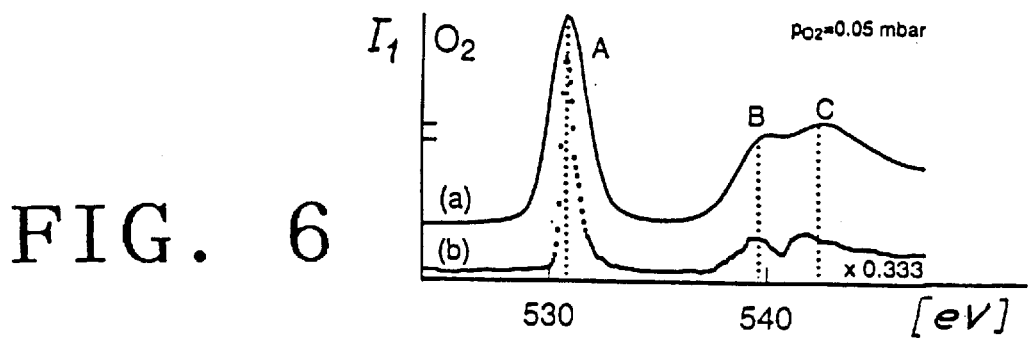

FIG. 6 shows by the upper curve (a) the spectrum of the current $I_1$ at the collector electrode 21 further from the sample for the same investigation conditions as applied for FIG. 4 ($P_{O2}$=0.05 mbar). The curve (b) shown below this shows, for comparison, a spectrum (with the ordinate dimension factor of 0.333) which was recorded with a known technique which is described by Ma et al in Phys. Rev. A44 (1991) page 1848. The distinctive intensive line A at about 531 eV corresponds to the ($1\sigma_u \to 1\pi_g^*$)—transition, while the broad double structure B, C at about 540.5 eV shows a* resonance transitions, a spin-up transition and a spin-down transition ($1\sigma_g \to 3\sigma_u^*$); the bipartition with the spacing approximately 2.5 eV is due to two different end state configurations of the spin.

In terms of shape and energy position of the observed lines, the spectrum (a) in FIG. 6 recorded with the apparatus of the present invention correlates well with the spectrum (b). This shows that the spectrum (a) is concerned with the same type of gas as the spectrum (c); the different line widths come about because of the different line widths of the monochrome X-ray radiation which is used. Saying this, it is demonstrated that the signal $I_1$ which is derived at the collector electrode 21 more remote from the sample with an apparatus according to the invention supplies a useful statement about the type of gas in the gas phase.

From the above examples it will be seen overall that the currents $I_1$, $I_2$ and $I_3$ can give information about X-ray absorption structures of the reactants of a gas-solid reaction both at and close to the surface of the solid as well as in the gas phase. Naturally, the invention is not limited to investigations of the particular materials used in the Examples given above, but can be utilized with success for the observation of any gas-solid reactions.

What is claimed is:

1. Apparatus for the investigation of the reactants involved in a reaction between a gas and a solid by means of X-ray absorption spectroscopy, comprising a measuring chamber (2) with a sample holder (23) for holding a sample (24) of the solid, means for creating an atmosphere of the gas in the measuring chamber at selectable pressure, a window (20) for the entry of X-rays for the irradiation of the sample (24), and a collector arrangement (21, 22) arranged spaced from the sample holder (23) for the collection of electrons released in the measuring chamber (2), wherein the collector arrangement comprises two collector electrodes (21 and 22) which are arranged spaced one following the other lengthwise along the X-ray path between the window (20) and the sample holder (23), and wherein each collector electrode (21, 22) and the sample holder (23) have respective connecting means (31, 32, 33) for the connection of each to a preselected potential and for the separate measurement of the currents ($I_1$, $I_2$, $I_3$) flowing through these connections.

2. Apparatus according to claim 1, wherein the structure and position of the collector electrode (22) which is closer to the sample holder (23) is such that it screens a mounted sample (24) in terms of effective measurement from electrons coming from the space between the two collector electrodes (21, 22), and it screens the other collector electrode (21) which is more remote from the sample effectively in terms of measurement from electrons coming from the space adjacent to the mounted sample (24).

3. Apparatus according to claim 1 or 2, in which each of the two collector electrodes (21, 22) surrounds the X-ray beam cross-section.

4. Apparatus according to claim 1 or 2, in which the collector electrode (22) closer to the sample comprises a plate whose plane extends substantially perpendicular to the X-ray path and which has an aperture for the passage of the X-rays directed towards the sample (24).

5. Apparatus according to claim 4, in which the collector electrode (21) which is more remote from the sample comprises a plate whose plane extends substantially perpendicular to the X-ray path and which is provided with an aperture for the passage of the X-rays directed towards the sample (24).

6. Apparatus according to one of the preceding claims, in which at least one of the collector electrodes (21, 22) comprises an electrode grating in the path of the X-rays which is penetratable by the X-rays.

7. Apparatus according to claim 6, in which the electrode grating is provided at the collector electrode (21) which is more remote from the sample.

8. Apparatus according to one of the preceding claims, in which the distance ($d_3$) measured in the beam direction between the surface of the sample which is irradiated by the X-rays and the collector electrode (22) which is closer to the sample lies within the range of about once up to about four times the distance ($d_2$) between the two collector electrodes (21, 22).

9. Apparatus according to claim 8, in which the said distance ($d_3$) is variable within the said range.

10. Apparatus according to claim 8 or 9, in which the distance ($d_1$) measured in the beam direction between the window (20) and the collector electrode (21) which is more remote from the sample lies within the range of about twice up to about three times the distance ($d_2$) between the two collector electrodes (21, 22).

11. Apparatus according to one of the preceding claims, in which the window (20) is penetrable by soft X-rays in the photon energy range of 100 up to 1000 eV.

12. Apparatus according to claim 11, in which the window (20) has a penetrability in the range of 2 to 60% for said soft X-rays.

13. Apparatus according to claim 12, in which the window (20) is of a polyimide foil which is coated on both sides with aluminum nitride and on the one side additionally with aluminum.

14. Apparatus according to claim 13, in which the polyimide foil of the window (20) is supported by a supporting grating of tungsten and polyimide.

15. Apparatus according to claim 7, in which the electrode grating is a copper grating coated with gold.

16. Apparatus according to claim 15, in which the fineness of the grating is about 40 lines per cm (100 lpi).

17. Apparatus according to claim 4, in which the plate of the electrode (22) which is closer to the sample comprises a nickel foil with an ultra-thin natural oxide coating.

18. Apparatus according to one of the preceding claims, in which the sample holder (23) contains a heating means (23c) for the controllable heating of the sample (24) within the range of up to about 1000° K.

19. Apparatus according to claim 18, in which the heating means (23c) is an electrical resistance heater in the form of a graphite plate.

20. Apparatus according to claim 18 or 19, in which the sample holder (23) comprises at least one metal clamp (25) which is arranged to hold the sample (24) in place and which is connected to the electrical connection means (33) of the sample holder (23).

21. Apparatus according to one of claims 18 to 20, in which the sample holder (23) is connected to a manipulator for the adjustment of the location and of the polar orientation of the sample.

22. Apparatus according to one of the preceding claims, in which the window (20) has connected in advance of it a UHV chamber (1) through which the X-rays are arranged to pass, and wherein a device (11) for the measurement of the intensity ($I_0$) of the X-rays directed towards the window (20) is provided in the UHV chamber.

23. Method for the investigation of the reactants involved in a reaction between a gas and a solid by means of X-ray absorption spectroscopy using the apparatus according to one of claims 1 to 22, in which:

a sample of the solid is arranged in the measuring chamber filled with the gas,

X-ray radiation is directed through the window onto a surface of the sample contacted by the gas, and respective electrical connections are made at respective preselected potentials to each collector electrode and to the sample, and the currents flowing through these three connections are measured separately and simultaneously and are then evaluated.

24. Method for the investigation of the reactants involved in a reaction between a gas and a solid by means of X-ray absorption spectroscopy using the apparatus according to one of claims 1 to 22, in which:

a sample of the solid is arranged in the measuring chamber filled with the gas,

X-ray radiation is directed through the window onto a surface of the sample contacted by the gas, and in order to investigate the X-ray structure of the reactants on and close to the sample surface, respective electrical connections at respective preselected potentials are made to the collector electrode closer to the sample and to the sample itself and the currents flowing through these two connections are measured separately and simultaneously and are then evaluated.

25. Method for the investigation of the reactants involved in a reaction between a gas and a solid by means of X-ray absorption spectroscopy using the apparatus according to one of claims 1 to 22, in which:

a sample of the solid is arranged in the measuring chamber filled with gas,

X-ray radiation is directed through the window onto a surface of the sample contacted by the gas, and in order to investigate the X-ray structure of the gas phase an electrical connection is made to the collector electrode which is more remote from the sample at a preselected potential and the current flowing through this connection is measured and evaluated.

26. Method according to one of claims 23 to 25, in which soft X-rays in the range of about 100 up to about 1000 eV are used.

27. Method according to one of claims 23 to 26, in which, for a spacing in the range of about 20 to 50 mm between the window and the sample and with an average intensity of the X-rays entering through the window in the range of $10^{10}$ up to $10^{11}$ photons per second, the gas atmosphere in the chamber is maintained at a total gas pressure of less than 25 mbar.

28. Method according to one of claims 23 to 27, in which a selected energy range of soft X-rays is traversed and the measured currents are recorded and evaluated as a function of the photon energy.

29. Method according to claim 28, in which for the evaluation of at least one of the measured currents the measured value of the respective current is divided by measurement values which have been derived before the investigation by measurement of the current derived from the collector electrode further from the sample during the traversing of the selected energy range of the X-rays under UHV conditions or under inert gas conditions.

30. Method according to claim 28 or 29, in which the intensity of the X-rays directed towards the window is measured and the evaluation of the currents is effected in relation to this intensity.

\* \* \* \* \*

UNITED STATES PATENT AND TRADEMARK OFFICE
CERTIFICATE OF CORRECTION

PATENT NO. : 6,212,253 B1
DATED : April 3, 2001
INVENTOR(S) : Thomas Schedel-Niedrig et al.

It is certified that error appears in the above-identified patent and that said Letters Patent is hereby corrected as shown below:

Item "[30] Foreign Application Priority Data", change "Mar. 3, 1998" to -- Mar. 11, 1998 --

Signed and Sealed this

Twentieth Day of November, 2001

*Attest:*

NICHOLAS P. GODICI
*Attesting Officer*   *Acting Director of the United States Patent and Trademark Office*